(12) United States Patent  
Axon et al.

(10) Patent No.: US 6,362,891 B1  
(45) Date of Patent: Mar. 26, 2002

(54) POWDER ANALYSIS

(75) Inventors: Tony Graham Axon; Stephen Victor Hammond, both of County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/519,902

(22) Filed: Mar. 7, 2000

(30) Foreign Application Priority Data

Mar. 9, 1999 (GB) ............................................. 9905318

(51) Int. Cl.[7] .......................... G01N 21/00; G01B 11/00
(52) U.S. Cl. ....................................... 356/433; 356/394
(58) Field of Search ................................. 356/300, 302, 356/303, 394, 433, 436, 440, 259.1, 239.2, 244, 246, 73; 250/573, 576, 577, 338.5, 339.01, 339.07, 339.08, 339.12; 436/164, 169, 170

(56) References Cited

U.S. PATENT DOCUMENTS

| 5,463,223 | A |   | 10/1995 | Wong et al. | ............ | 250/339 R |
| 5,470,757 | A | * | 11/1995 | Gagnon et al. | ............. | 436/164 |
| 5,675,410 | A | * | 10/1997 | Kanda | ........................ | 356/244 |

FOREIGN PATENT DOCUMENTS

| EP | 0767369 | 4/1997 |
| GB | 2292798 | 3/1996 |
| GB | 2328016 | 2/1999 |

* cited by examiner

Primary Examiner—Frank G. Font  
Assistant Examiner—Michael P. Stafira  
(74) Attorney, Agent, or Firm—Peter C. Richardson; Gregg C. Benson; Carl J. Goddard

(57) ABSTRACT

A method of analysing powder formed as a mixture of pharmaceutical ingredients and derived from a bulk preparation of powder by spectrophotometric analysis utilising transmission measurements. A sample powder is removed from the bulk mixture and pressed into a test wafer and spectrophotometrically analysed for the transmitted beam to provide an assay test spectrum of actual absorption characteristics of ingredients in the material of the wafer. These characteristics of the assay test spectrum are compared with predetermined assay standard spectra determined from individual standard wafers for each relevant ingredient in the powder mixture by measuring absorption characteristics of the individual ingredients from the transmitted beam at known wavelengths of the beam to assess acceptability of the homogenity and distribution of the relevant ingredient in the powder of the sample. The wafer is preferably pressed with flat and parallel opposed end faces through which the beam is directed.

12 Claims, 5 Drawing Sheets

POWDER ANALYSIS

CROSS-REFERENCE TO RELATED APPLICATIONS

Figure 1:
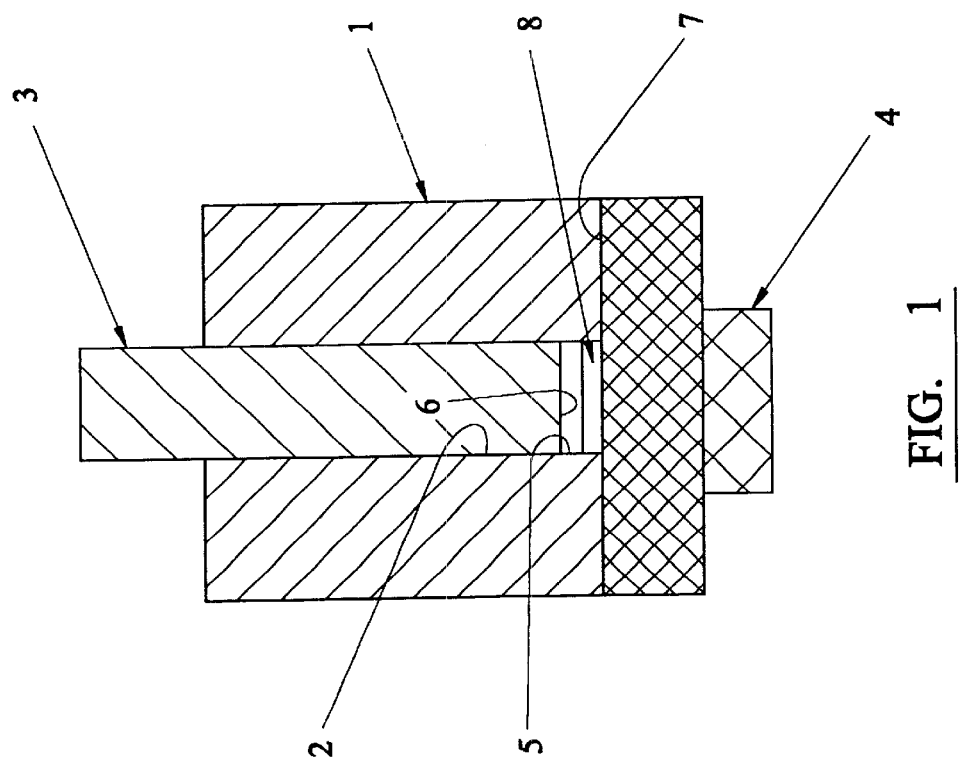

This application is filed claiming priority under 35 U.S.C. §119 to British Application GB 9905318.3, filed Mar. 9, 1999.

TECHNICAL FIELD AND BACKGROUND ART

The present invention relates to powder analysis and is particularly concerned with a method of analysing powder formed as a mixture of ingredients and derived from a bulk preparation of such a powder.

The present invention was primarily, but not essentially, developed for use in the pharmaceutical industry where it is conventional practice in the commercial production of a product which is, or is to be derived from, a powder for the ingredients of that powder to be loaded into a mixing chamber where they are tumbled or otherwise agitated to ensure thorough mixing of the ingredients. For a pharmaceutical product, the powdered ingredients loaded into the chamber will be one or more active ingredients and one or more excipients. In a typical pharmaceutical facility, the bulk powder mixture will be in the order of 1000 kg and will be intended for sub-division, usually into small containers convenient for retail purposes, into capsules for individual doses of the powder or for processing into individual dose tablets.

Irrespective of the manner in which the bulk powder from the mixing chamber is subsequently processed to be presented for use or retail purposes, in the pharmaceutical industry there are statutory requirements that the ingredients in the form of the pharmaceutical or chemical constituents in end product (typically powder, capsules, or tablets as aforementioned) as presented for retail purposes or use are dispersed uniformly throughout the material of the end product to ensure that dose formulations are identical within prescribed tolerances.

As a consequence, pharmaceutical products derived from powder are subjected to a qualitative and quantitative control analysis, principally to ensure that the end product has required chemical constituents, that the proportions of the required chemical constituents are correct and that the chemical constituents are dispersed uniformly throughout the end product. Where the bulk powder is processed into individual dose tablets, a conventional form of quality control is to subject tablets randomly selected from a production batch to spectrophotometric analysis where a beam of electromagnetic radiation (usually near infrared—NIR) is directed to and transmitted through the selected sample tablet for the transmitted beam to be detected and analysed. From variations in the absorption characteristics exhibited by the ingredients (chemical/pharmaceutical constituents) of the tablet to the applied radiation beam as measured by the detector, it is possible in known manner to effect the required qualitative and quantitative analysis.

Techniques for analysing tablets by NIR spectrophotometric transmission measurements are disclosed in our patent specification EP-A-0,896,215 and in EP-A-0767369.

Once production has started to sub-divide a bulk powder mixture into discrete weights or doses and to package those doses typically into capsules or to press them into tablets, production rates are so fast that if analysis of the final product indicates that the ingredients, particularly active ingredients, are not uniformly dispersed throughout the bulk powder mixture, there is likely to be considerable wastage and expense (both in materials and in production), in the products which were made prior to a decision to stop production.

As a consequence (and in some countries it is a statutory requirement in the production of pharmaceutical products from powder mixtures), it is conventional practice to analyse samples of powder derived from the bulk mixture in the mixing chamber to ensure appropriate homogenity and concentration of the active and excipient ingredients within the bulk mixture before its sub-division commences. For this analysis several powder samples are taken from the bulk mixture at locations spaced from each other and at various depths in the mixture to give an overall picture of how well the ingredients are homogenised throughout the blend or mix.

Each powder sample that is removed from the bulk powder mixture is assessed for homogenity of its ingredients and conventionally this is achieved by either of two well-known techniques. The longest standing and probably most utilised technique is that of high performance liquid chromatography (HPLC) which is well-known in the art and as such need not be discussed in detail. However despite its popularity, it is recognised that HPLC has distinct disadvantages notably a) it utilises toxic solvents and therefore it has to be used in a facility remote from the chemical/pharmaceutical manufacturing facility for good manufacturing practice, b) the analysis can take many hours or days by experienced personnel with consequent expense and delays in production time, and c) it is suitable only for determining concentration throughout the mixture of the or a particular active ingredient in the mixture.

The second technique is spectrophotometric analysis of the powder sample by reflectance measurements of a near infrared (NIR) beam. For each sample, a tablet dose weight is weighed into a glass vial or other container and the sample is then scanned. The sample is then mixed and scanned again—this procedure is repeated five times and the resultant spectra are then averaged. Spectrophotometric analysis of powder by reflectance measurements is discussed in connection with our patent publication WO 95/00831. The tablet dose weight is used for the analysis (although up to three times such a dose weight is permitted for the analysis) in accordance with regulations laid down by recognised pharmaceutical bodies on the basis that if a much larger weight from the sample is used, it could suggest that a mixture is properly homogenised when in fact it is not. The sample is scanned five times due the nature of the depth of penetration of the NIR light beam. Tests have shown that using standard NIR reflectance optics, the NIR beam will only pass into a fine white powder up to a depth of 0.5 mm. As a consequence, to get a representative view and useable cross section of the whole sample, the powder has to be mixed and scanned five times and the resultant spectra averaged. Homogenity of the mixture is then usually determined by calculating the standard deviation of the samples at absorption characteristics which are unique to the active ingredient or ingredients. The numerous scanning and re-mixing of powder from each sample is a lengthy procedure which causes consequential delays in production and is preferably carried out by experienced laboratory personnel. Overall therefore this second technique of analysis is generally regarded as expensive and of suspect accuracy due to the inability of the NIR beam to scan efficiently a relatively thick surface layer of powder.

From the foregoing, it will be realised that there is a need to provide a method of analysing powder formed from a mixture of ingredients and prepared in bulk (particularly but not essentially for pharmaceutical and/or chemical products) and which method alleviates the disadvantages of the above described prior proposals. It is an object of the present invention to satisfy this need. More particularly, the present invention has as its aims to provide a method of analysing powder formed as a mixture of ingredients and derived from a bulk preparation which permits a fast analysis that may be used efficiently by inexperienced personnel to alleviate personnel error and delays in production and to provide an accurate analysis on the basis of which an assessment can be made on the acceptability or otherwise of the homogenity and concentration of either or both active ingredients and excipients in the bulk powder mixture or blend.

STATEMENT OF INVENTION

According to the present invention, there is provided a method of analysing powder formed as a mixture of ingredients and derived from a bulk preparation thereof which comprises predetermining an assay standard spectrum for a relevant ingredient of the bulk powder mixture by spectrophotometrically analysing characteristics of that relevant ingredient from transmission measurements of a beam of electromagnetic radiation applied to and passing through the relevant ingredient to provide a spectrum of absorption characteristics at known wavelengths of the beam; removing a sample of powder from the bulk mixture and pressing powder of the sample into a self-supporting test wafer; spectrophotometrically analysing characteristics of the material of the test wafer from transmission measurements of the beam of electromagnetic radiation applied to and passing through the wafer to provide an assay test spectrum of actual absorption characteristics of ingredients in the material of the test wafer for known wavelengths of the beam, and comparing absorption characteristics from said assay standard spectrum with said assay test spectrum at predetermined wavelengths of the beam to assess acceptability of the relevant ingredient in the powder of the sample.

By the present invention, sample powder removed from the bulk mixture of powder ingredients as prepared for subsequent processing is subjected to spectrophotometric analysis by a beam of electromagnetic radiation (usually and hereinafter referred to as near infrared—NIR) that is transmitted through the material of the powder sample following that material being compressed into a self-supporting wafer.

The self-supporting characteristics of the wafer are intended so that the wafer may be handled relatively freely for fitting into the spectrometer without disintegrating and to avoid the possible interference of glass supports in the spectrum obtained. Typically the wafer will be formed with powder from an extracted sample amounting to approximately 0.5 to 1.5 (preferably 1.0) dose weight of tablets or capsules which may be intended to be produced from the bulk powder material. This powder dose weight may quickly and easily be compressed into a wafer utilising a simple barrel and cylinder moulding press so that the wafer may be formed by unskilled operatives. Similarly such an unskilled operative may locate the wafer in a wafer holder of a spectrometer and actuate the spectrophotometric system to provide the required assay test spectra.

Relevant ingredients, be they either active or excipient, in the bulk powder mixture will be known and each relevant ingredient is subjected to spectrophotometric analysis to provide an assay standard spectrum. This assay standard spectrum is preferably achieved by use of a self-supporting standard wafer of the respective relevant ingredient similarly sized to the test wafer formed from the bulk powder sample. By comparing the assay test spectrum of the actual absorption characteristics of ingredients in the material of the test wafer formed from the sample of the bulk powder material with the assay standard spectra of the relevant ingredients it is possible to assess the quantitative presence of the relevant ingredients in the powder sample. This latter assessment may also be made by unskilled personnel quickly and efficiently.

It is also possible to provide the required assay standard spectrum from a sample of powder which includes the relevant ingredient and which sample has already been determined as being accurate in the quantity and distribution of the relevant ingredient, for example, by HPLC. This validation of the accuracy of the spectroscopy by comparison with chromotographical testing is likely to require skilled personnel, but having once determined the assay standard spectrum that data is available for use by unskilled personnel in carrying out the method of the present invention.

In practice, it will be usual for an operative to remove two or more samples of powder from spaced locations (both horizontally and vertically) in the bulk mixture and to press similar self-supporting wafers from the samples and to provide assay test spectra for the respective wafers. Absorption characteristics from the assay standards are then compared with the respective assay test spectra at appropriate wavelengths of the beam to assess acceptability of the distribution and the concentration of the relevant ingredients throughout the bulk mixture. It will be appropriate for experienced or skilled personnel to determine permissible tolerances in the distribution of the relevant ingredients but once these have been set, it is possible for an unskilled operator to quickly determine whether the homogenity of the distribution of respective ingredients throughout the bulk powder mixture is acceptable for that mixture to proceed to further processing such as tableting or encapsulation of individual dose weights.

The method of the present invention will permit analysis of the bulk powder mixture to be effected by unskilled personnel quickly and efficiently in the vicinity of a production facility for good manufacturing practice thereby alleviating considerable expense which may otherwise be incurred from lengthy delays in production frequently caused by use of conventional analysis techniques.

A preferred feature of the present invention is that the powder of the sample is pressed into a wafer having flat, parallel and opposed end faces and that the NIR beam is directed perpendicularly through those flat end faces. Such a flat faced wafer is advantageous in that it provides efficient transmission characteristics for the NIR beam to be effective over a wide band wavelength in the spectrum of the transmitted beam. In comparison, conventional tablets tend to have convexly curved opposed end faces on which may be embossed or engraved trade marks or other indicia and when such tablets are subjected to spectrophotometric analysis by transmission it is found that the resultant spectrum from the transmitted beam is useable over a relatively narrow wavelength band due to light scatter and stray light resulting from the convex and possibly undulating profile presented by the opposed end faces of the tablet.

Furthermore, by use of a flat faced wafer, it is convenient and efficient to mount the wafer in a holder of the spectrometer with flat faces in face to face contact to alleviate stray light from the applied or incident NIR beam from being directed into the detector between the wafer and the wafer holder (rather than by passing through the material of the wafer).

A further advantage of the present invention is that in a production facility where the bulk powder mixture is to be processed into tablets, the spectrometer and detector as used for the analysis of the material in the wafer derived from the powder sample can also be used for spectrophotometric analysis of tablets produced from the powder mixture in accordance with the disclosure in our patent specification EP-A-0,896,215.

DRAWINGS

Figure 4:
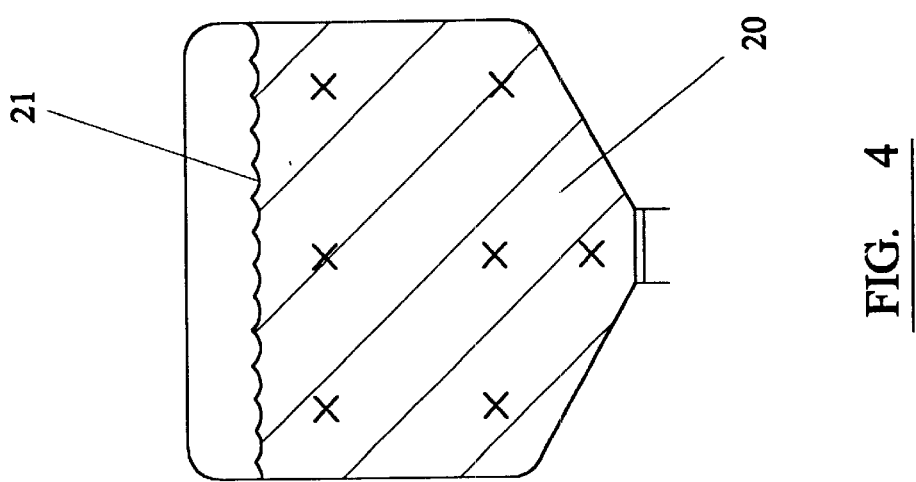
Figure 2:
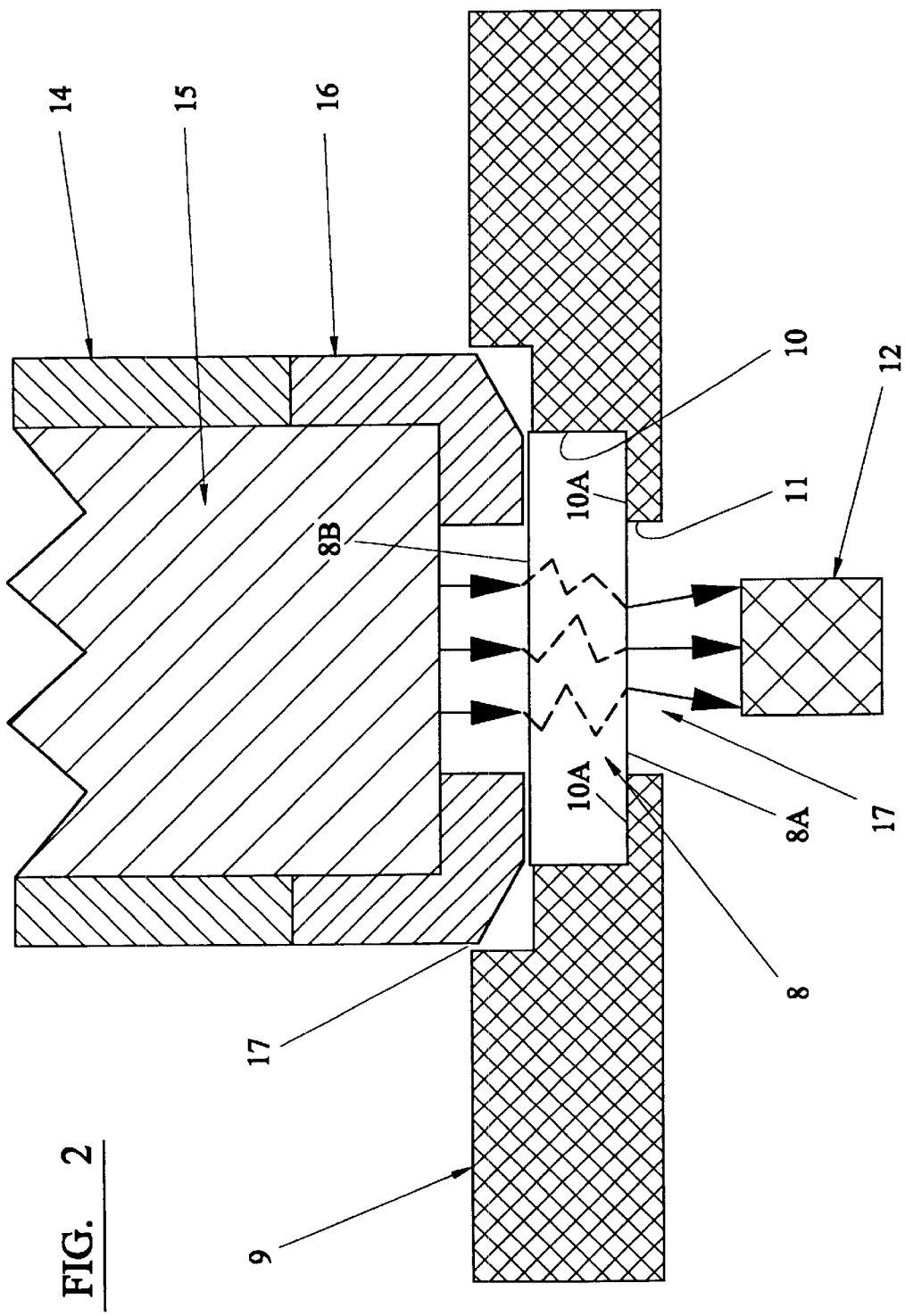
Figure 3:
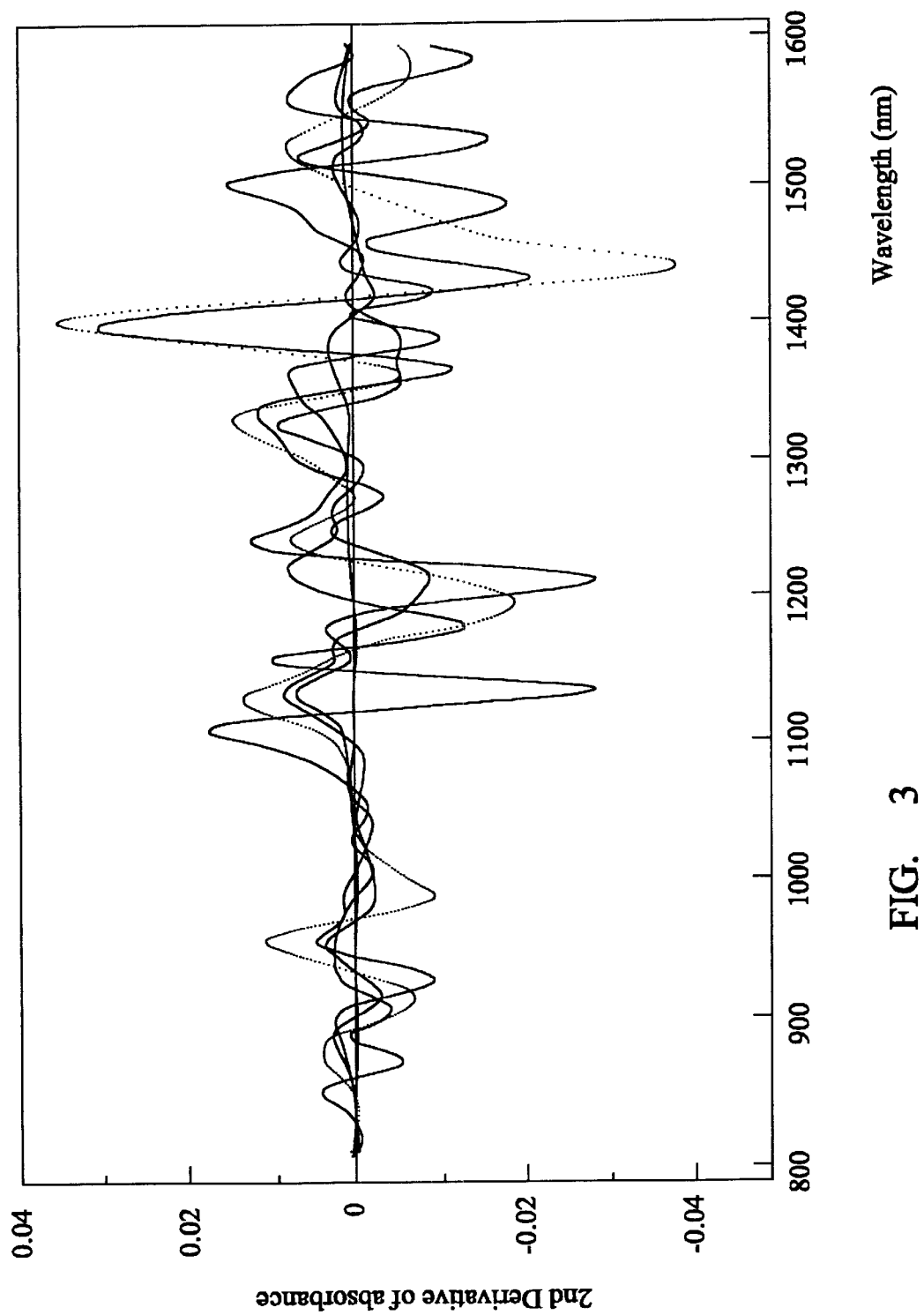
Figure 3A:
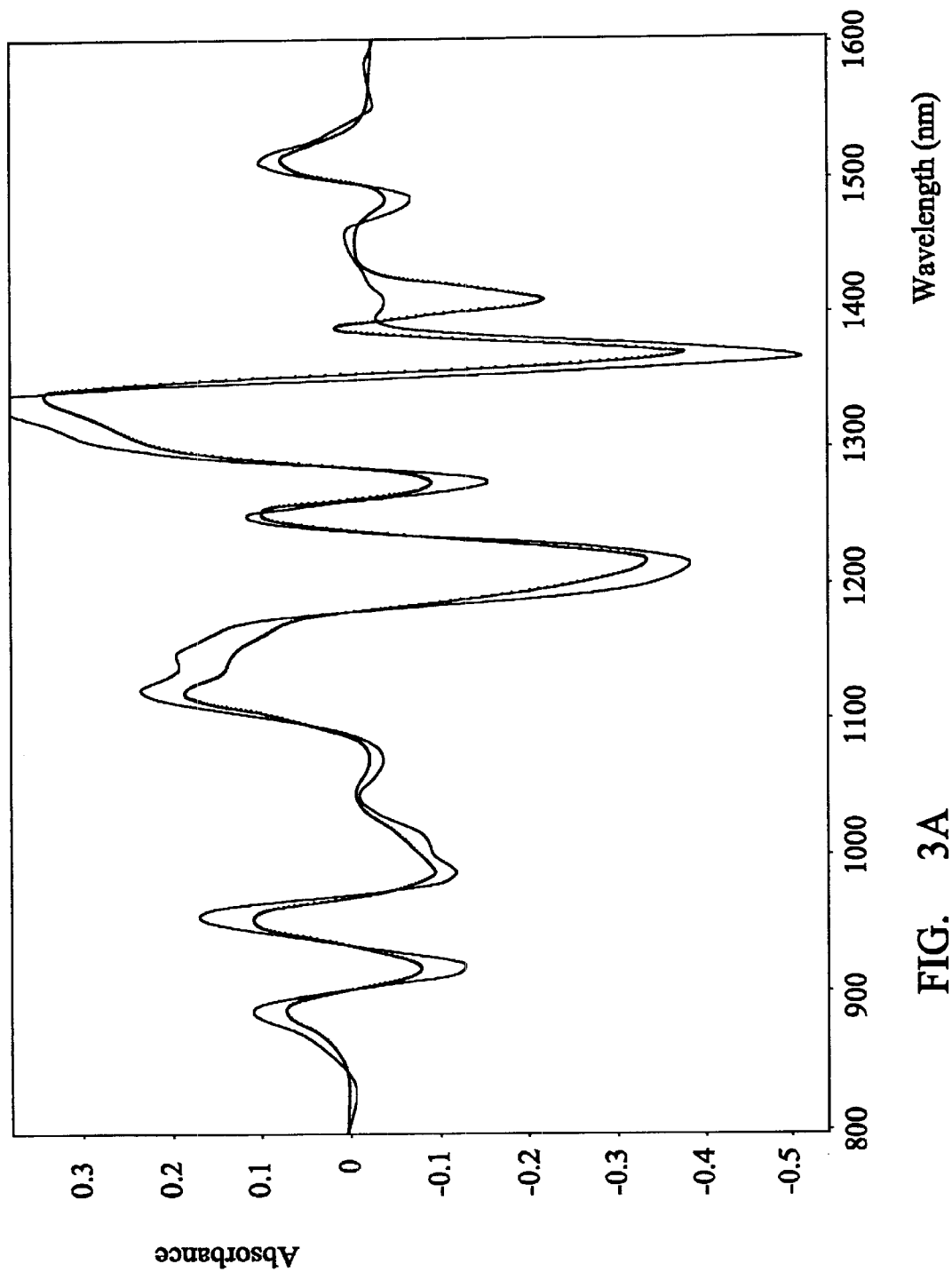
Figure 6:
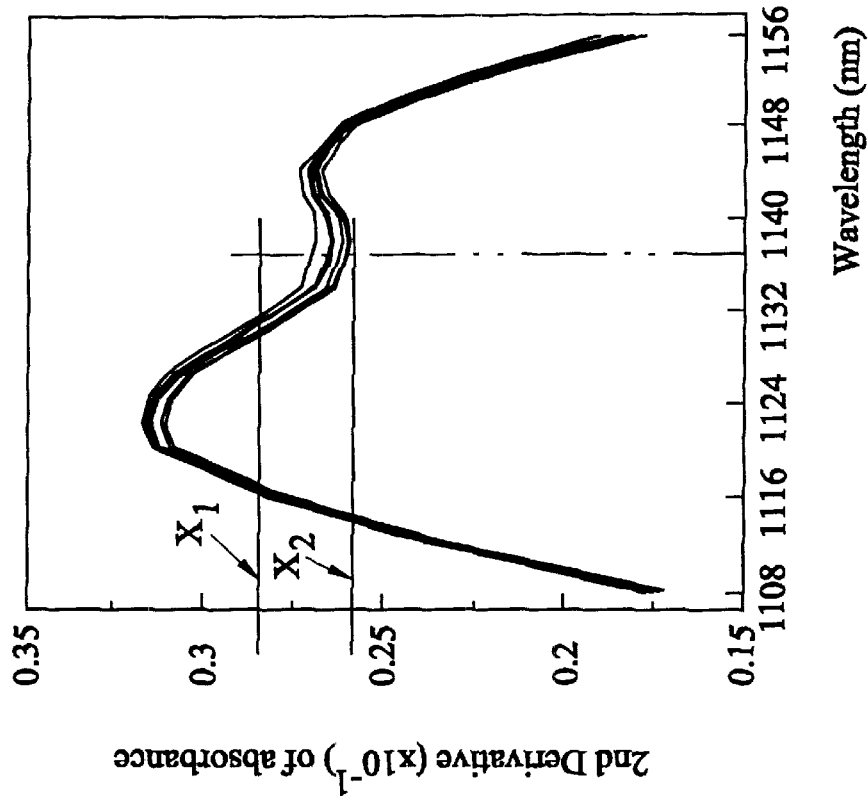
Figure 5:
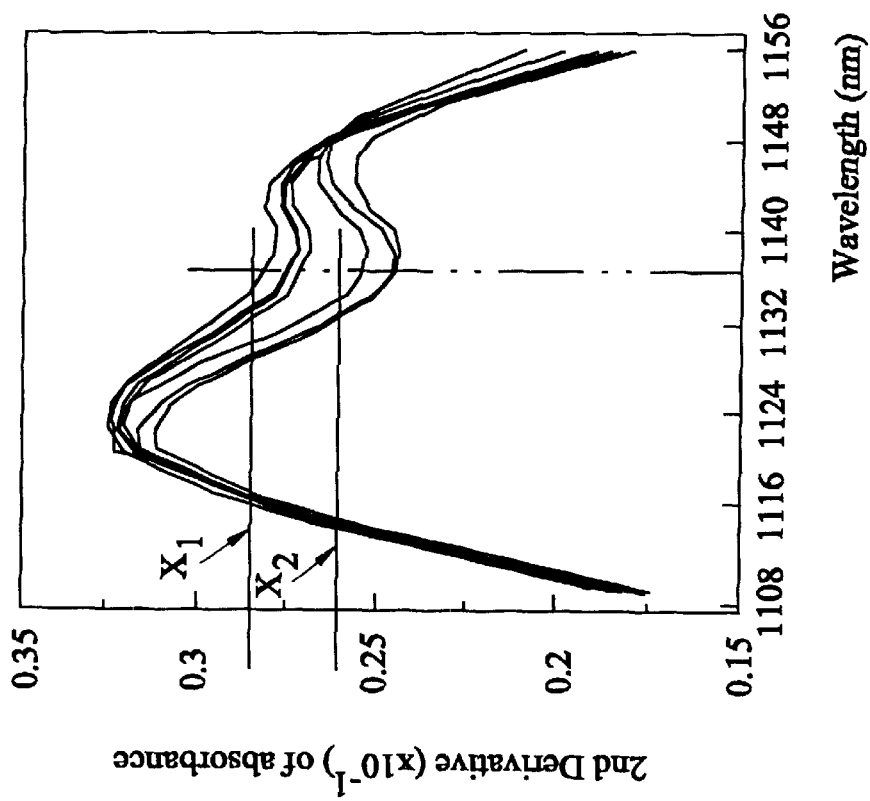

An embodiment of the method of analysing powder in accordance with the present invention will now be described by way of example only, with reference to the accompanying illustrative drawings in which:

FIG. 1 diagrammatically shows part of a moulding tool for forming a wafer to which the method of the invention is to be applied;

FIG. 2 diagrammatically shows a side elevation, in part-section, of a spectrophotometer for use in analysing characteristics of a wafer derived from the mould of FIG. 1;

FIG. 3 shows absorption spectra for individual relevant ingredients in a bulk powder mixture which is to be analysed in accordance with the method of the invention;

FIG. 3A compares absorption spectra derived from a wafer and from a tablet pressed from the same sample powder;

FIG. 4 diagrammatically illustrates powder in a bulk mixing chamber and indicates typical locations at which seven samples of the powder are taken for analysis;

FIG. 5 shows absorption spectra which may be derived from eight wafers formed from the powder samples taken from the mixing chamber of FIG. 4 and which samples are considered to be unacceptable for ingredient distribution; and FIG. 6 shows absorption spectra similar to that of FIG. 5 and which permits a conclusion that ingredient distribution throughout the powder mixture is acceptable.

DETAILED DESCRIPTION OF THE DRAWINGS

The present invention utilises spectrophotometric analysis by transmission of ingredients in a wafer 8. The wafer is formed by compression of sample powder derived from a bulk powder mixture and for the purpose of forming the wafer 8 from powder by a non-skilled operative, a simple moulding tool is provided and shown in FIG. 1. The mould has a barrel 1 within a through cylinder 2 of which is slidably located a complementary cylindrical plunger 3. The plunger 3 projects from one end of the cylinder 2 and the opposite end of the cylinder is closed by a removable base 4. A cylindrical moulding chamber 5 is thus defined within the cylinder 2 between a flat radially extending end face 6 of the plunger 3 and an opposing flat parallel face 7 of the base 4.

The wafer 8 is formed by removing the plunger 3 from its cylinder 2 and loading into the cylinder 2 a predetermined weight of powder from which the wafer 8 is to be formed. The powder is distributed uniformly over the face 7 within the cylinder 2 and the plunger 3 inserted into the cylinder for its flat end face 6 to lie on the powder.

The assembly as shown in FIG. 1 is now fitted within the jaws of a press or torque wrench (not shown) by which the plunger 3 is driven along its cylinder towards the base 4 to compress the powder into the wafer 8. It is intended that the wafer 8 when removed from the moulding chamber 5 (simply by opening that chamber on removing the base 4 from the barrel 1) should be self-supporting so that if it can be handled reasonably freely for mounting in a spectrometer. To provide self-supporting wafers from typical pharmaceutical powders, it is preferred that the powder is subjected to a compressive force of at least 175 kg per square centimetre, more preferably 211 kg per square centimetre.

The wafer when removed from the press will have a cylindrical profile with parallel and opposed flat end faces which extend perpendicularly from the axis of the cylinder. The cylinder 2 will usually have a diameter in the range of 0.8 to 2.5 cm as considered appropriate for the amount of sample powder which is to be loaded into the moulding chamber 5 so that the wafer will be of adequate thickness to be self-supporting.

FIG. 2 diagrammatically shows part of a spectrophotometer for analysing characteristics of the material of the wafer 8 by measurements from a beam of near infrared radiation (NIR) transmitted through the wafer. Conveniently, the spectrophotometer will be considered as that sold under the trade mark INTACT™ of Foss Electric. The spectrophotometer has a wafer holder 9 with a cylindrical recess 10 which is complementary to the cylindrical form of the wafer 8 and which recess 10 is co-axial with a circular aperture 11 in the wafer holder. Sited below the aperture 11 is a detector 12 from which spectra measurement signals are derived in known manner. The cylindrical recess 10 is concentric with a cylindrical probe 14 housing a fibre-optic bundle 15 through which the NIR beam is to be directed from its source. The probe 14 is longitudinally displaceable in the direction of its axis for its tip 16 to be received as a close sliding fit in a cylindrical recess 17 in the wafer holder which recess 17 is concentric with and extends from the recess 10. A wafer 8 which is to be subjected to analysis is located in the complementary recess 10 with one of its flat end faces 8a in face to face abutment with a flat annular bottom face 10a presented in the bottom of the recess 10.

For an analysis measurement, the probe tip 16 is moved into face to face abutment with the second flat face 8b of the wafer 8 following which a beam 17 of NIR radiation is directed from the probe tip to be transmitted through the wafer by way of its flat end faces 8a and 8b to be applied to the detector 12 and provide measurements from which absorption spectra of the wafer material are derived.

From FIG. 2, it will be seen that the complementary seating of the wafer 8 in its cylindrical recess and in face to face abutment with the annular bottom face 10a alleviates stray light from passing between the wafer and its holder to the detector 12. The face to face abutment between the probe tip 16 and the wafer 8 also alleviates stray light passing through the wafer to the detector. Whilst the force of abutment between the probe tip and wafer may be light, it should be ensured that the self-supporting characteristics of the wafer are adequate for the wafer to withstand the abutment without material disintegration. This abutment will also urge the wafer into abutment with the face 10a of the wafer holder.

The method of the present invention was developed primarily for analysing pharmaceutical powder to determine whether or not active ingredients and possibly excipients in the powder are distributed uniformly/homogeneously throughout the bulk of the powder. This is achieved by reference to absorption spectra derived from the transmission of the NIR beam 17 through wafers 8 formed from samples of the bulk powder mixture per se and by reference to similar absorption spectra from assay standard wafers each of which is for a relevant ingredient of the bulk powder mixture. In the present example, it may be assumed that the bulk powder mixture has five relevant ingredients comprising one active and four excipients such as a sugar, a phosphate, a glycolate and a sterate. Five wafers 8 are produced one for each of these five relevant ingredients.

Usually the assay standard wafers as aforementioned will be formed from a weight of the relevant ingredient approximating to the dose weight of tablets or capsules into which the bulk powder mixture is to be processed. Each of the assay standard wafers 8 of the relevant ingredients is then subjected to analysis by the spectrophotometer shown in FIG. 2 to provide a spectrum showing variations in absorption by the relevant ingredient of the NIR beam for different wavelengths. These absorption characteristics are mathematically treated in known and conventional manner to provide a second derivative which can be plotted against wavelength.

FIG. 3 shows five graphs, one for each of the wafers of the five relevant ingredients in the bulk powder mixture under consideration to provide an assay standard spectra. It will be seen from FIG. 3 that the useful assay standard spectra extends over a broad band of wavelength (800 to 1600 nm) in the NIR beam and this is believed to be attributable, to a substantial extent, by use of flat parallel faces of the wafer through which the beam is transmitted to the detector so that this transmission may be achieved efficiently (particularly in the absence of stray or spurious light). The provision of such a usefully wide or broad band spectrum as shown in FIG. 3 has the advantage that a wide range of wavelengths can be studied for absorption characteristics of active or excipient ingredients in the test wafer under consideration. It will be noted from FIG. 3 that different ingredients may peak predominately over other ingredients in a second derivative of their absorbance at different wavelengths so that these distinctive peaks can be utilised to provide readily discernable points in the assay standard spectra against which assay test spectra derived from samples of the bulk powder material may be compared.

Advantages of using flat faced wafers 8 as aforementioned will also be appreciated from FIG. 3A which shows two graphs of absorbance against wavelength. Graph A (chain dotted line) is the spectrum derived by the transmission of the NIR beam through the flat faced wafer formed from a powder sample as previously described. Graph B (uniform line) is the spectrum derived by the transmission, in similar circumstances, of the NIR beam through a conventional shape of tablet pressed from the powder sample, the tablet being of a lozenge shape with opposed part convex faces having bevelled edges. The opposed faces of the tablet were embossed with a trade mark and dosage weight respectively. The tablet and wafer wave of substantially the same weight. It will be apparent that the deviation of absorbance for the wafer (Graph A) is less than that for the tablet (Graph B). This indicates that the absorption demonstrated by the tablet can be too strong to permit adequate light transmission for accurate measurement. For certain wavelengths, particularly larger IR wavelengths as shown by Graph B, it is unlikely that any light will be transmitted through the tablet—this is partly due to the non-flat profile which the faces of the tablet present to the NIR beam and the resultant scatter effect which the tablet shape produces. In comparison, scatter is very much reduced for the flat faced wafer and it is possible to determine the thickness of the wafer to permit a wider range of wavelengths transmission (and therefrom provide a broader useful spectrum) in comparison with that provided by the tablet.

FIG. 4 shows a mixing chamber 20 which is loaded with the previously mentioned five relevant ingredients/components in the proportions and weights as may be required for the pharmaceutical/chemical mixture, particularly for non-pharmaceutical applications where regulations may permit. The powders in the chamber 20 are thoroughly mixed by tumbling or otherwise to provide a bulk powder mixture in which it is necessary for the relevant ingredients to be dispersed uniformly and homogeneously throughout the mixture 21 prior to that mixture being further processed to provide single dose tablets or capsules. In a typical pharmaceutical production process, the powder mixture 21 may amount to 1000 kg.

For analysis purposes, several samples of powder 21 are now removed from the bulk mixture at various spaced locations throughout the breadth and depth of the bulk powder. Typically seven samples will be taken from the powder 21 at locations indicated by the small crosses in the mixing chamber 20 so that such samples should provide a fair representation of the manner in which the relevant ingredients are dispersed throughout the whole of the bulk mixture 21. Preferably, each of the samples corresponds approximately to the dose weight of the tablet or capsule which is intended to be formed from the bulk powder, typically 0.25 grams, although such samples are likely to be in the range of 0.22 to 1.0 grams. The powder of the seven samples taken as aformentioned is formed into seven discrete test wafers 8 as previously described. Each test wafer from the sample is then subjected to spectrophotometric analysis in a similar manner to the analysis of the standard wafers for the individual relevant ingredients to provide assay test spectra of the absorption characteristics for various wavelengths in the NIR beam.

A particular advantage of analysing the material of the standard and test wafers spectrophotometrically by transmission of the NIR beam through the thickness of the wafer is that it provides accurate spectra which is indicative of the ingredients throughout the thickness of the wafer so that, in practice, it is only necessary to scan each wafer once in the spectrometer (as compared with the minimum of five scans required when analysing powder spectrophotometrically by reflectance techniques).

FIG. 3 shows that the spectrum for one of the five ingredients has a prominent absorption peak for the beam wavelength 1136 nm and this peak is conveniently used as a reference for that particular ingredient in carrying out the analysis. From the assay test absorption spectra of actual absorption characteristics of the seven test wafers derived from the samples of bulk powder as shown in FIG. 5 (which is conveniently over a narrow band wavelength which includes the 1136 nm relevant wavelength), it will be seen that at the 1136 nm wavelength, the lines of the spectra extend over the absorbant range 0.024 to 0.028. Although only six spectral lines are shown at the 1136 nm wavelength whilst seven spectral lines would be expected from the seven assay test wafers, it will be appreciated that two of the spectral lines are substantially coincident with each other (as indicated by the presence of a relatively thick line).

For the particular ingredient whose absorbance characteristic peaks at the 1136 nm wavelength, it is determined, empirically or otherwise, that for such ingredient to be homogeneously and uniformly dispersed throughout the bulk powder mixture, it is necessary for its second derivative of absorbance (as shown by the spectra of FIG. 5) to be within the tolerance range 0.026 to 0.028 (as indicated by the lines X1 and X2 in FIG. 5). The spectra of FIG. 5 clearly indicate that the spread of absorbance demonstrated by the ingredient relevant to the 1136 nm wavelength from the seven samples within the bulk powder mixture falls well outside of the acceptable tolerance range indicated by the lines X1 and X2 so that bulk powder mixture is unacceptable for further processing.

This conclusion may be determined quite readily and quickly by unskilled personnel instructed in the preparation of the test wafers, the loading of these into the spectrometer and the interpretation of spectra produced similar to that shown in FIG. 5. The operative can then, if necessary, submit the bulk powder to further mixing and prepare a further set of assay test wafers to provide further assay test spectra until such spectra may be similar to that shown in FIG. 6 where, at the 1136 nm wavelength, all of the spectral lines are within the absorbance tolerance range between the lines X1 and X2 indicating that, at least as far as the particular relevant ingredient as aforementioned is concerned, the homogenity and uniformity of the mixture is acceptable.

It will be appreciated that all five of the relevant ingredients from which the spectra of FIG. 3 was produced will be assessed similarly from the seven test wafers to ensure that the homogenity and uniformity of all five relevant ingredients throughout the bulk powder mixture is acceptable.

As a consequence of the present invention, it is possible for unskilled personnel quickly, efficiently and economically to:

1) essentially identify that the correct product or ingredient is present in the bulk powder mixture by ensuring that the specific absorption characteristics (for example the peak at 1136 nm in FIG. 3) for that product appear in the assay test spectrum;

2) show that the concentration of the relevant ingredient is as required from the intensity of the absorption indicated in the assay test spectrum for that ingredient (for example the intensity indicated by the aforementioned peak at 1136 nm); and 3) assess how well the relevant ingredient has been mixed (homogenity) throughout the bulk powder mixture from variations in the absorbance at predetermined wavelengths for identical wafers produced from several samples of powder taken throughout the bulk powder mixture (for example the seven samples assessed at the aforementioned peak of 1136 nm in FIGS. 5 and 6).

What is claimed is:

1. A method of analysing powder formed as a mixture of ingredients and derived from a bulk preparation thereof which comprises predetermining an assay standard spectrum for a relevant ingredient of the bulk powder mixture by spectrophotometrically analysing characteristics of that relevant ingredient from transmission measurements of a beam of electromagnetic radiation applied to and passing through the relevant ingredient to provide a spectrum of absorption characteristics at known wavelengths of the beam;

removing a sample of powder from the bulk mixture and pressing powder of the sample into a self-supporting test wafer;

spectrophotometrically analysing characteristics of the material of the test wafer from transmission measurements of the beam of electromagnetic radiation applied to and passing through the wafer to provide an assay test spectrum of actual absorption characteristics of ingredients in the material of the test wafer for known wavelengths of the beam, and comparing absorption characteristics from said assay standard spectrum with said assay test spectrum at predetermined wavelengths of the beam to assess acceptability of the relevant ingredient in the powder of the sample.

2. A method as claimed in claim 1 and comprising pressing the powder of the sample into a wafer having substantially flat and parallel opposed end faces through which said beam is directed.

3. A method as claimed in claim 2 which comprises pressing the wafer as a cylinder with opposed flat and parallel end faces of the cylinder lying in radially extending planes perpendicular to the axis of the cylinder.

4. A method as claimed in claim 3 in which the cylindrical wafer has a diameter in the range of 0.8 to 2.5 cm.

5. A method as claimed in claim 1 in which the bulk powder mixture is to be processed into predetermined dose weights by tableting or encapsulation and which comprises forming said wafer from sample powder having a weight in the range substantially corresponding to 0.5 to 1.5 said dose weight.

6. A method as claimed in claim 5 in which said dose weight is in the range of 0.2 to 1.0 grams, preferably 0.25 grams.

7. A method as claimed in claim 1 which comprises pressing powder of the sample to a pressure in the range of 175 to 246 kg per square centimetre, preferably 211 kg per square centimetre, to form the wafer.

8. A method as claimed in claim 1 in which the beam is derived from a probe tip and which comprises moving the probe tip into abutment with the self-supporting wafer for transmission of the beam through the wafer.

9. A method as claimed in claim 1 in which the beam transmitted through the wafer is directed through an aperture to detector means for measurement and which comprises locating the wafer to overlie the aperture with a peripheral marginal edge part of a flat end face of the wafer extending beyond the aperture and being in face to face abutment with a flat face of a wafer holder to alleviate stray light from passing between the wafer and the wafer holder to the detector means.

10. A method as claimed in claim 1 which comprises removing at least two samples of powder from spaced locations in the bulk mixture, pressing similar test wafers from the samples, providing assay test spectra for the respective test wafers and comparing absorption characteristics from said assay standard spectrum with said respective assay test spectra at predetermined wavelengths of the beam to assess acceptability of the distribution and/or concentration of the relevant ingredient throughout the bulk mixture.

11. A method as claimed in claim 1 which comprises predetermining at least two said assay standard spectra, one for each of a corresponding number of predetermined relevant ingredients in the bulk powder mixture, and comparing absorption characteristics from said respective assay standard spectra with said assay test spectrum at predetermined wavelengths of the beam to assess acceptability of the respective relevant ingredients in the powder of the sample.

12. A method as claimed in claim 1 in which the, or each, relevant ingredient in the powder is an active ingredient or an excipient.

* * * * *